United States Patent [19]

Neti et al.

[11] 4,063,895
[45] Dec. 20, 1977

[54] METHANE ANALYZER

[75] Inventors: Radhakrishna Murty Neti, Brea; Ray Lawrence Roggenkamp, Fountain Valley, both of Calif.

[73] Assignee: Beckman Instruments, Inc., Fullerton, Calif.

[21] Appl. No.: 704,268

[22] Filed: July 12, 1976

[51] Int. Cl.² ............... B01J 1/10; G01N 21/26
[52] U.S. Cl. ................... 23/232 R; 23/254 R; 250/432 R; 250/527; 204/162 R
[58] Field of Search ............ 23/232 R, 232 E, 254 R, 23/254 E, 254 R, 255 E; 250/373, 432–438, 527; 204/162 R

[56] References Cited
U.S. PATENT DOCUMENTS

| 854,965 | 5/1907 | Potter | 250/527 X |
| 1,969,655 | 8/1934 | Mailey | 250/527 X |

Primary Examiner—Robert M. Reese
Attorney, Agent, or Firm—Robert J. Steinmeyer; Paul R. Harder; Donald A. Streck

[57] ABSTRACT

A reactor for removing contaminants such as reactive hydrocarbons from the gas being sampled by gas component determination apparatus is disclosed. A confined path is disposed adjacent a high purity quartz lamp capable of generating low order wavelengths. By selecting the flow rate of the sample gas past the quartz lamp in the presence of ozone, all hydrocarbons can be photo-oxidized or all hydrocarbons with the exception of methane. Apparatus is also disclosed employing the reactor wherein the methane content of a sample gas can be determined. The sample gas is alternately measured as to the quantity of all hydrocarbons contained therein and then measured for methane. The difference between the two readings is indicative of the amount of non-methane hydrocarbons present.

14 Claims, 5 Drawing Figures

ABSORPTION SPECTRA OF SOME PARAFFIN HYDROCARBONS; (1) METHANE [CH₄(g)]: (2) ETHANE [C₂H₆(g)]: (3) PROPANE [C₃H₈(g)]: (4) PERDEUTERO-N-BUTANE [n-C₄D₁₀(g)]: (5) n-BUTANE [n-C₄H₁₀(g)].

ABSORPTION SPECTRA OF SOME PARAFFIN HYDROCARBONS; (1) METHANE [$CH_4(g)$]; (2) ETHANE [$C_2H_6(g)$]; (3) PROPANE [$C_3H_8(g)$]; (4) PERDEUTERO-N-BUTANE [$n-C_4D_{10}(g)$]; (5) n-BUTANE [$n-C_4H_{10}(g)$].

4,063,895

METHANE ANALYZER

BACKGROUND OF THE INVENTION

With increased interest in problems of air pollution, particularly as to pollutants caused by combustion of hydrocarbons, there has been a rapid increase in the research directed to improved gas sampling apparatus. Apparatus for determining the content of a specific component in a sample stream is, ideally, designed to be responsive only to the component of interest. Unfortunately, such apparatus often responds not only to the component of interest, but to various "contaminants"0 as well. Where such contaminants exist within the sample stream, they must be removed, neutralized, or their effects masked. Since much of the gas being tested is the atmosphere which we breathe and the atmosphere often contains numerous hydrocarbons, these hydrocarbons become one of the major contamination sources. They need to be measured in the exhaust emissions of automobiles as well, in order to improve fuel efficiency and minimize emissions. According to the guidelines established by the Environmental Protection Agency, methane is the only nonreactive hydrocarbon; all others are considered reactive hydrocarbons. Presently, methane is analyzed either by a gas chromatograph using flame ionization detection, an infrared analyzer, or by selective thermal cracking of other hydrocarbons. Gas chromatographic analysis is not continuous, requires at least five minutes for each analysis cycle, and is, therefore, not suitable for modal analysis in automobile engine research and development. Infrared analysis, by its very nature, is not selective in spite of the extreme refinements in detectors and optical filters used, as serious interference occurs from other hydrocarbons. Selective thermal cracking is claimed to yield non-quantitative data due to the changing nature of the catalyst.

Accordingly, it is the object of the present invention to provide a reactor capable of removing the effects of all hydrocarbons from a gas sample stream or all hydrocarbons except methane, to provide apparatus for removing hydrocarbons as contaminants from a gas sample stream or, alternatively, to provide the ability to test for methane content as an item of interest within the gas stream.

It is a further object of the present invention to provide a reactor capable of removing the effects of a family of contaminants from a gas sample stream being used by gas analysis apparatus for the determination of specific components of the gas sample stream.

SUMMARY

The above objects are achieved by the reactor which is the subject of the present invention wherein an enclosed space is provided through which the gas sample is passed. A source of light energy is provided in the enclosed space, emitting light energy including wavelengths approaching but not less than 147 nm. The light source further is formed of a high purity quartz so that the light energy will be rich in 184.9 nm wavelength light. In the preferred embodiment, the sample is passed through a passageway existing as a gap of 0.125 inches adjacent the surface of the lamp. Additionally, means are provided to assure that the sample contains at least 2% saturated vapor pressure of moisture before entering the reactor. In operation, a source of oxygen is mixed with the sample and the sample/oxygen mixture is passed through the reactor. The light energy puts the hydrocarbon molecules into a superactivated state and, simultaneously, converts the oxygen to ozone which then combines with the superactivated hydrocarbon molecules.

DESCRIPTION OF THE PREFERRED EMBODIMENT

Figure 1:
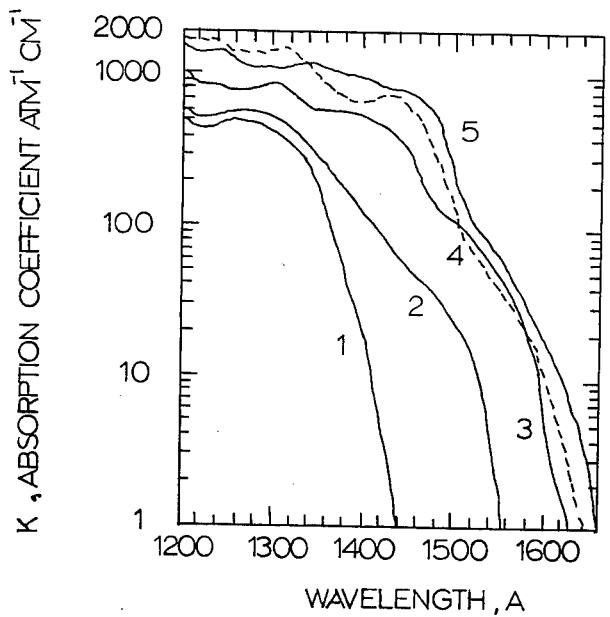
FIG. 1 is a graph showing the wavelength at which various hydrocarbons absorb ultraviolet light.

Reference to the literature suggests that methane does not absorb any light energy of wavelength longer than 147 nm as graphed in FIG. 1. All other hydrocarbons absorb light of wavelengths longer than 147 nm to varying degrees. Photochemical studies of hydrocarbons were made with ultraviolet sources capable of generating light in the 90–123.6 nm wavelength region of the electromagnetic spectrum. From these observations it was postulated that, upon absorbing light energy, methane and other hydrocarbons are photolyzed into organic radicals and hydrogen. The radicals generated depend upon the hydrocarbon being investigated.

The light sources used in these earlier investigations were generally of high intensity arc, spark discharge or windowless discharge sources filled with hydrogen or rare gases. Quartz mercury lamps are known to be rich in the generation of 253.7 nm mercury line and transmit some 184.9 nm line. High purity quartz mercury lamps are known to generate considerably more of 184.9 nm light. Quartz as processed by Hearaus Quarzschmelze, GmbH, Hanau, West Germany and imported and distributed by Amersil, Inc. of Sayreville, N.J. under the name Supracil is of extremely high purity and transmits a maximum of the 184.9 nm line. All the evidence suggests that methane, ethane and some other hydrocarbons are not photochemically activated with light of wavelengths longer than 147 nm. Yet, the greatest known spectral line generated from high purity quartz lamps such as the Supracil quartz mercury lamp, is light of 184.9 nm. Thus, it follows that a Supracil quartz mercury lamp should not be able to photolyze methane.

Light of 184.9 nm photo-disassociates $O_2$ into oxygen atoms to generate ozone. The oxygen atoms are highly reactive. It was felt that oxygen atoms and/or ozone might react with some of the hydrocarbons and not react with methane. With this assumption in mind, a U-shaped Supracil type 21 quartz mercury lamp 4 inches long was constructed. The diameter of the Supracil tubing used was 9–8 mm. The lamp was housed in either a polytetrafluoroethylene or aluminum housing 5.75 inches long with an internal diameter of 1.2 inches. A polytetrafluoroethylene or aluminum insert was then introduced so that the gas sample passes through this gap between the lamp wall and the insert. The gap is about 0.06 inch. The construction of the reactor is described in greater detail hereinafter.

Figure 2:
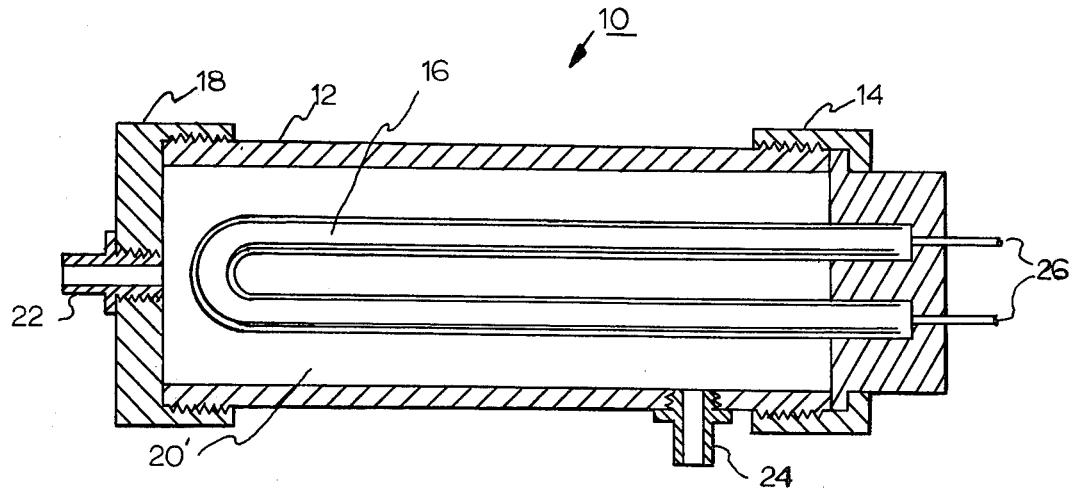
FIG. 2 is a cross section of a reactor constructed according to the teachings of the present invention.

Referring first to FIG. 2, a standard ozone producing cell 10 is shown comprising a body 12 having a first cap 14 closing one end of body 10 and supporting the quartz lamp 16. A second cap 18 is disposed to close the opposite end of body 12 to create an enclosure 20 having quartz lamp 16 therein. An inlet pipe 22 and an outlet pipe 24 are provided in cap 18 and body 12 to allow the introduction of a gas into enclosure 20 through inlet pipe 22 and the exit thereof from outlet pipe 24. When appropriate power (e.g. 3000V, 30 ma a.c.) is supplied to quartz lamp 16 through wires 26 attached thereto, quartz lamp 16 is caused to emit the wavelengths which are characteristic of the lamp according to its construction. A cell 10 such as that shown in FIG. 2 employing a Supracil quartz lamp is routinely employed in apparatus manufactured by the assignee of this application for the generation of ozone. The lamp employed therein is manufactured for the assignee, Beckman Instruments, Inc., according to proprietary techniques but is available as Beckman Instruments Part No. 630888. The subject lamp was specifically designed to optimize the output of ozone through its use. Incidentally, however, it has been found that in addition to its superior ozone producing characteristics, it also possesses certain additional characteristics in regard to its emitted wavelengths which, when operated in a non-standard manner, make it particularly well suited for use in a hydrocarbon reactor. Consequently, by controlling the environment wherein it is used and the flow rate of a test gas passed thereby, it is possible to use the subject lamp to selectively photolyze all hydrocarbons with the exception of methane. Additionally, completely unexpected results in relation to methane were achieved which will be hereinafter described.

Figure 3:
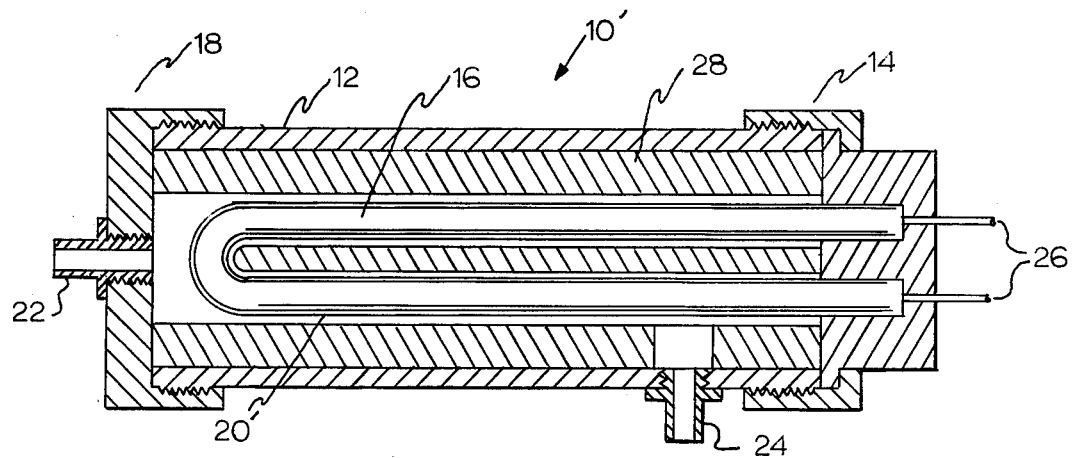
FIG. 3 is a cross section of the preferred embodiment of a reactor according to the teachings of the present invention employing an insert to create a confined space adjacent the quartz lamp for the passage of the gas through the reactor.

Referring now to FIG. 3, the preferred embodiment of the present invention when used as a hydrocarbon/methane reactor is shown. A reactor 10' comprises the elements of the basic ozone cell 10 of FIG. 1 and, additionally, employs spacer element 28 disposed within enclosure 20 to create the restricted enclosure 20' adjacent quartz lamp 16 as shown through which the gas passes. The creation of enclosure 20' with spacer element 28 serves two purposes. First, the surface temperature of the quartz lamp 16 is elevated to an estimated 300+ C. This elevated temperature at the surface of quartz lamp 16 appears to modify the wavelength of the light adjacent the surface of quartz lamp 16. Second, any test gas entering inlet pipe 22 and passing through enclosure 20' to exit through outlet pipe 24 will be constrained to pass close adjacent the surface of quartz lamp 16. The combined effect of the inherent properties of the Supracil quartz lamp coupled with the addition of spacer element 28 to form the restricted passage of enclosure 20' serves to create a reactor with a high propensity for the photolyzation of hydrocarbons and having wavelengths approaching those which tend to photolyze methane. Consequently, at low volume flow, all hydrocarbons including methane passing through the reactor 10' will be photooxidized. This, of course, is completely contrary to what would be expected from the data of FIG. 1. On the other hand, at higher volume flows, all the hydrocarbons will be photo-oxidized with the exception of methane which will be photo-oxidized to a lesser, predictable, and constant degree. This unexpected characteristic can be employed to good advantage as will be hereinafter described in greater detail. It is to be understood that the cell 10 of FIG. 3 employing the Supracil quartz lamp will achieve the unexpected results of photo-oxidizing methane if the flow rate is slow enough. Contemporary requirements, however, require small sample sizes and fast responses which have been achieved by the configuration of the preferred embodiment of the present invention.

Figure 4:
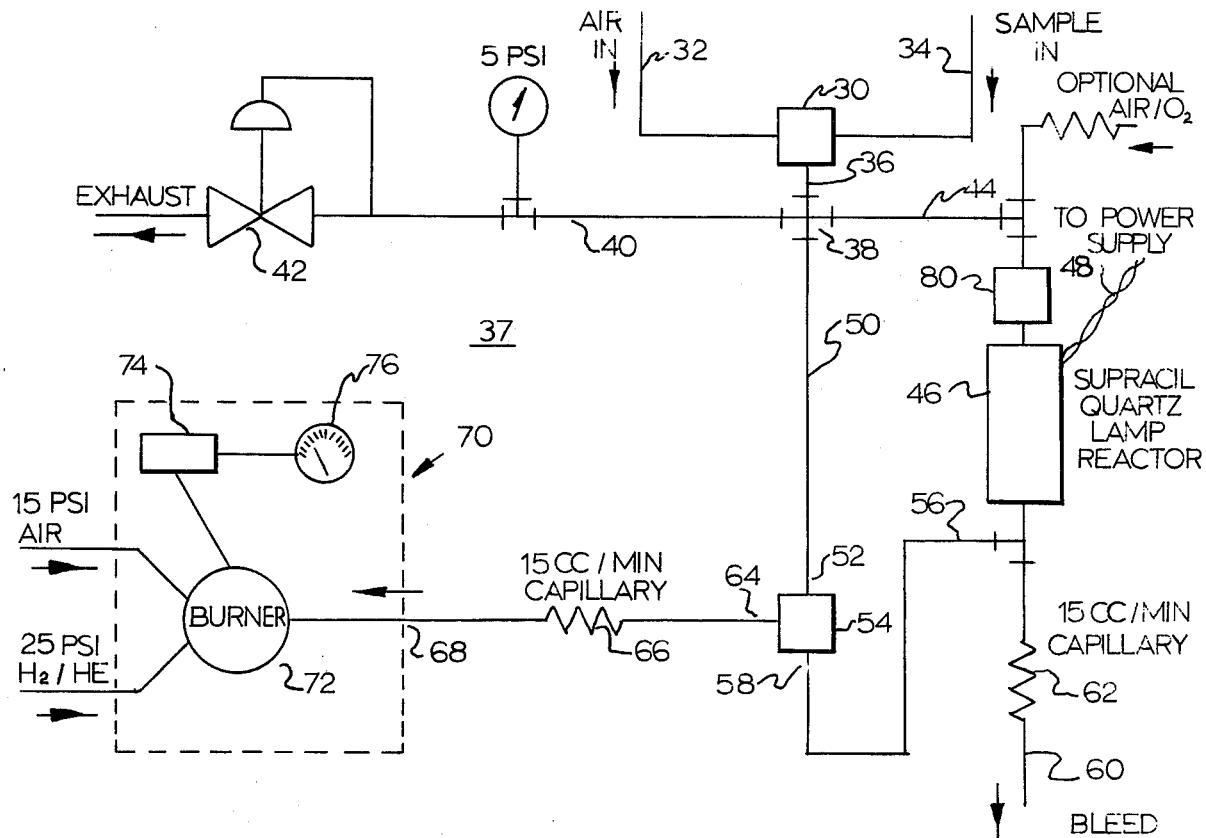
FIG. 4 is a system employing the reactor of the present invention for determining the quantity of methane in a sample stream.

Apparatus as used to test the present invention and also usable as a methane analysis system is shown in FIG. 4. A two position first valve means 30 is connected with one input 32 connected to an air supply (not shown) and the second input 34 connected to means for supplying the sample gas (not shown). The output 36 of first valve means 30 is the input to the system generally labeled 37. Output 36 connects into three lines through a common coupling 38. The first line is exhaust line 40 containing pressure regulation means 42 which maintains a constant pressure within system 37. The second line is reactor input line 44 which is the input to a reactor 46 such as that of FIG. 3. Reactor 46 is connected to an appropriate power supply (not shown) by wires 48. The third of the three lines input to by output 36 is reactor bypass line 50, which is connected to one input 52 of a two position second valve means 54. The output of reactor 46 is connected by reactor output line 56 to the second input 58 of second valve means 54. A bleed line 60 containing an appropriate capillary 62 therein is connected into reactor output line 56 between reactor 46 and input 58 of second valve means 54 to allow the flow rate through reactor 46 to be adjusted. The output 64 of second valve means 54 is connected through an appropriate capillary 66 to the sample input 68 of a gas analysis instrument 70 generally indicated by the dashed box (such as a Beckman Model 400 Hydrocarbon Analyzer). In a hydrocarbon analyzer being instrument 70, a sample gas is burned in burner 72. Appropriate electronic means 74 detect the ionization which occurs in burner 72 and translate the amount of ionization into an equivalent ppm value which is displayed on meter 76.

When using the apparatus of FIG. 4 for hydrocarbonmethane analysis, first valve means 30 is first switched to input 32 so that air (containing no hydrocarbons) will be input to system 37 and the zero level on the hydrocarbon analyzer instrument 70 set in a manner appropriate to the instrument employed. First valve means 30 is then switched to input 34 to accept samples being supplied thereto. First valve means 30 is, of course, only a convenience item and sample/air inputs could be applied directly into coupling 38 by removable lines to the various input sources. With the sample being applied to system 37, second valve means 54 is then used to cause the sample gas to pass through reactor 46 or bypass it by switching to input 58 for gas through reactor 46 or input 52 to bypass. When doing methane analysis, the bleed line 60 is set at a rate which will allow the complete photo-oxidation of all hydrocarbons except methane and a proportional photo-oxidation of methane. With second valve means 54 switched to the input 52 position a first reading is then made with instrument 70 which is the total hydrocarbon content of the sample. Second valve means 54 is then switched to the input 58 position and a reading taken on the sample now having passed through reactor 46. This reading is proportional to the methane content of the sample and must be rescaled to full value. The exact rescaling factor will vary from reactor to reactor and on the bleed rate so that the reactor/bleed combination should be calibrated using a known methane content sample. In a fixed and calibrated system set up for a particular constant use, the rescaling could be included in electronic means 74 so that the ppm reading on meter 76 would be an indication of the full value instead of the proportional value. It was also found, as will be apparent from the experimental data that follows hereinafter, that while the results would duplicate on a fixed sensitivity scale of instrument 70, switching from scale to scale makes it preferred to verify the calibration in each new position and use the approprite rescaling factor for each range for optimum accuracy of results.

It will be obvious that if total hydrocarbon content and non-methane hydrocarbon content are not items of interest, a simplified system for measuring methane alone could be constructed by inserting the sample at reactor input line 44 and connecting reactor output line 56 directly to capillary 66 and thence to input 68 of instrument 70.

It should also be obvious that an analysis instrument 70 other than that for detecting hydrocarbons can be used with the reactor of the present invention as well. In such a case, the bleed 60 is adjusted for a slower passage rate through reactor 46 which will photo-oxidize all hydrocarbons including methane. Thus, by passing the sample gas through the reactor 46 before entry into the instrument 70, the sample gas will be scrubbed of all "contaminant" hydrocarbons. It has been found in this regard that the reactor also effects other possible "contaminants" to a gas analysis system. For example, it has been ascertained that NO is photo-oxidized by the Supracil quartz lamp reactor.

The operability of the present invention for its intended purpose was tested in a number of experiments using the apparatus of FIG. 4. Initially, a sample of 10 ppm methane in air was made. This sample was used to set the span of a Beckman Model 400 Hydrocarbon Analyzer, which was used throughout the experiments. The Model 400 Hydrocarbon Analyzer ranges are marked according to its response to methane. If samples containing other hydrocarbons, saturated or unsaturated, are used, the response is different from a methane sample. For example, a 100 ppm hexane sample will give a response of 600 ppm of methane whereas a 100 ppm sample of benzene will give a response of less than 600 ppm of methane due to the double bonds in the benzene structure. For purposes of this disclosure, only the reduction due to the photo-oxidation is of concern. The sample flow rate used was about 10 cc/min at a pressure of 5 psi. After the span was set, the response due to other hydrocarbons was similarly determined. After testing the response due to various hydrocarbons directly, the hydrocarbon test gases were then passed through the specially built Supracil quartz mercury lamp reactor at flow rates between 10–90 cc/min. At a flow rate of 25 cc/min the results were:

| Hydrocarbon Sample | Response Direct | Through Photolyzer | Range |
|---|---|---|---|
| 10 ppm methane in air | 26 | 17 | 25 ppm |
| 100 ppm ethane in air | 84 | 6 | 100 ppm |
| 100 ppm ethylene in air | 68 | 0 | 100 ppm |
| 100 acetylene in air | 94 | 0 | 100 ppm |
| 100 ppm benzene in air | 79 | 0 | 250 ppm |
| 50 ppm methane in $N_2$ | 27.5 | 19 | 100 ppm |

From the above experimental results, it appeared that though the mercury lamp does not generate light of wavelengths shorter than 184.9 nm, it was able to partially photolyze methane. This is quite contrary to the currently known observations. This photolysis was dependent upon the residence time, suggesting that it is the synergistic effect of high temperature in the immediate vicinity of the lamp, the presence of ozone, and UV light photolyzing methane and other hydrocarbons and further oxidizing them to $CO_2$ and $H_2O$. By careful selection of the residence time and lamp operating conditions, it is possible to selectively analyze methane and photo-oxidize all the other hydrocarbons into products not detected by the flame ionization hydrocarbon analyzer.

While it is impossible to fix the exact reaction that takes place within the reactor, the evidence from numerous experiments using various configurations of the reactor leads to certain conclusions which are felt to be accurate. The initial experiments using a standard ozone generator employing a Supracil quartz lamp and flow rates far below normal confirmed the unexpected results of the photolyzation of methane. The next step was the insertion of a polytetrafluoroethylene spacer element such as that of FIG. 3, labeled 28. The results were as hoped. The confined space adjacent the lamp allowed vastly increased flow rates while attaining good photolyzing characteristics. Since earlier experiments employing a Pen Ray lamp made from GE 204 double bore quartz had been completely unsuccessful in the photolyzing of methane, it was felt that, somehow, the Supracil quartz mercury lamp was emitting wavelengths shorter than 147 nm. Subsequent discussions with the importer of the Supracil quartz, however, lead to the conclusion that this was highly unlikely.

To test the possibility that, in fact, the heat of the lamp was causing the polytetrafluoroethylene spacer element to break down chemically and the fluorine was attacking the methane, an aluminum spacer element was constructed. The aluminum spacer element was designed with a separate piece to fit snugly into the "U" of the lamp. It was hoped that the more confined path adjacent the lamp would provide superior results. Exactly the opposite took place. Virtually no photo-oxidation took place. The insert between the "U" of the lamp was removed and the reactor tried again. The results were again as with the polytetrafluoroethylene spacer element. This proved two things. First, of course, it was not fluorine attacking the methane since there was no polytetrafluoroethylene present to decompose the methane. More important, however, it indicated that it was a combination of the Supracil quartz lamp and ozone that was necessary to achieve the desired results since a sufficient volume in which to develop ozone was the only change made. Combining all these facts, it is believed that the following takes place. The Supracil quartz mercury lamp emits wavelengths greater than 147 nm, but closer thereto than other quartz is capable of achieving. This, combined with the effect of the hot surface of the lamp superactivates the methane molecules approaching the point where photolyzing would take place yet never achieving it. This superactivation of the methane molecule does, however, render the molecule susceptible to oxidation by the ozone generated simultaneously from the oxygen present in the gas stream. This is further borne out by the results of example #6 discussed in greater detail hereinafter. Thus, in the reactor of the present invention, methane is photo-oxidized even in the absence of complete photolizing or fracturing of the methane molecules by the light energy.

By way of further illustration the following experiments were made:

| 1) | Sample 100 ppm Benzene in Air | 1000 ppm Range |
|---|---|---|
| | Response in dark | 33.5 |
| | Response in light at 80 cc/min bleed rate | 22.5 |
| | Response in light 15 cc/min bleed rate | 13.3 |
| | Response in light at 2 cc/min bleed rate | 7.0 |
| | Response in light 1 cc/min bleed rate | 6.5 |
| 2) | Sample 100 ppm Benzene plus 10 ppm Methane in Air | 250 ppm Range |
| | Response in dark | 60.5 |
| | Response in light at 80 cc/min bleed rate | 7.5 |
| | Response in light at 15 cc/min bleed rate | 2.0 |
| | Response in light at 2 cc/min bleed rate | 2.0 |
| | Response in light at 1 cc/min bleed rate | 2.0 |
| 3) | Sample 100 ppm Ethane in Air | 100 ppm Range |
| | Response in dark | 88 |
| | Response in light at 80 cc/min bleed rate | 50.4 |
| | Response in light at 15 cc/min bleed rate | 18.5 |
| | Response in light at 2 cc/min bleed rate | 3.5 |
| | Response in light at 1 cc/min bleed rate | 1.0 |
| 4) | Sample 10 ppm Methane in Air | 10 ppm Range |
| | Response in dark | 47 |
| | Response in light at 80 cc/min bleed rate | 44.5 |
| | Response in light at 15 cc/min bleed rate | 40.0 |
| | Response in light at 2 cc/min bleed rate | 32.0 |
| | Response in light at 1 cc/min bleed rate | 30.5 |
| 5) | Sample 100 ppm Acetylene in Nitrogen | 100 ppm Range |
| | Response in dark | 51.5 |
| | Response in light at 80 cc/min bleed rate | 27.5 |
| | Response in light at 15 cc/min bleed rate | 15.5 |
| | Response in light at 2 cc/min bleed rate | 6.0 |
| | Response in light at 1 cc/min bleed rate | 4.0 |
| 6) | Sample 100 ppm N-Hexane in Nitrogen | 250 ppm Range |
| | Response in dark | 96 |
| | Response in light at 80 cc/min bleed rate | 85 |
| | Response in light at 15 cc/min bleed rate | 72 |
| | Response in light at 2 cc/min bleed rate | 52 |
| | Response in light at 1 cc/min bleed rate | 48.5 |

Example 6 seems to deviate from the expected result in that only 50% total photo-oxidation is observed instead of the 100% desired. This result is quite proper, however, and goes to validate the postulated theory of operation of the present invention. It should be noted that the carrier gas in this example was nitrogen. Being a commercial grade of nitrogen, it can be anticipated that the gas contained trace amounts of oxygen on the order of 10 ppm. Thus, the amount of ozone which could be generated was minimal. To further verify this conclusion, a known amount of air of about 10 cc/min was blended with the sample. With the addition of this source of oxygen, the photo-oxidation of normal hexane in nitrogen was complete, thus supporting the deduced theory of operation of the reactor. This also points out the need to assure that ozone exists in excess within the reactor for proper operation. By so doing, the amount of methane photo-oxidation becomes solely a function of its flow rate through the reactor.

| 7) | Sample About 500 ppm Methane in Air | 250 ppm Range |
|---|---|---|
| | Response in dark | 95 |
| | Response in light at 80 cc/min bleed rate | 83.5 |
| | Response in light at 15 cc/min bleed rate | 74.5 |
| | Response in light at 2 cc/min bleed rate | 56.5 |
| | Response in light at 1 cc/min bleed rate | 52.0 |
| 8) | The Above Sample Passed Over Water Layer at Ambient Temperature | 250 ppm Range |
| | Response in dark | 94.5 |
| | Response in light at 80 cc/min bleed rate | 73.5 |
| | Response in light at 15 cc/min bleed rate | 55.5 |
| | Response in light at 2 cc/min bleed rate | 31.5 |
| | Response in light at 1 cc/min bleed rate | 26.5 |
| 9) | Sample 100 ppm Ethane plus 1% Oxygen in Nitrogen | 250 ppm Range |
| | Response in dark | 99 |
| | Response in light at 80 cc/min bleed rate | 61.5 |
| | Response in light at 15 cc/min bleed rate | 25 |
| | Response in light at 2 cc/min bleed rate | 3 |
| | Response in light at 1 cc/min bleed rate | 2 |

The above results amply illustrate that most of the hydrocarbons can be photo-oxidized with the Supracil quartz mercury lamp in the presence of oxygen. The photo products are further oxidized to $CO_2$. This was established by measuring the gradual increase of $CO_2$ on a Beckman Model 865 Infrared Analyzer sensitized for $CO_2$.

To prove or disprove the uniqueness of the Supracil quartz in the mercury lamp of the reactor, a duplicate lamp was manufactured employing GE 204 quartz. When 100 ppm ethane in 1% $O_2$ + $N_2$ was passed through a reactor incorporating this lamp at flow rates that achieved 100% photo-oxidation with the Supracil quartz, only about 90% photo-oxidation was achieved. This result was as expected by the time the test was conducted and further goes to prove the postulated theory of operation. Both the Supracil and GE 204 are high purity quartz and, therefore, able to pass more of the low order wavelengths approaching 147 nm than standard quartz. The Supracil quartz, however, because of its higher purity vis-a-vis the GE 204 quartz, is richer in these low order wavelengths. Thus, with the Supracil quartz representing 100%, it follows that lesser purity quartz lamps will transmit proportionally less of the low order wavelengths resulting in proportionally less activation of the molecules with an attendant reduction in the amount of photo-oxidation at a fixed flow rate. To use a reactor employing a GE 204 quartz lamp, therefore, the flow rate need only be slowed slightly to again achieve 100% photo-oxidation.

In actual operation, the sample of a mixture of hydrocarbons is passed through the ultraviolet reactor with a bleed rate of 1-2 cc/min. The total sample flow through the reactor remains at about 15 cc/min. In order to achieve rapid response time, the total sample flow through the rest of the system may be up to 3 l/min or more depending upon the sample handling lines and their volumes. The effluent sample from the reactor is fed to the burner to determine the methane content of the sample. The analyzer is spanned with a known sample of methane. Then the test gases may be analyzed according to the method described here.

This method is, of course, not restricted to the detection by the flame ionization method. It can successfully be used with any other method of detection. To illustrate the technique, the response due to the above-mentioned hydrocarbons was determined in a Beckman Model 865 Infrared Analyzer, sensitized for methane analysis. Then the response on the infrared analyzer was determined after photo-oxidizing the samples in the above-described reactor. Before photo-oxidation, the analyzer showed significant response from benzene. The response due to benzene was completely eliminated as the sample was photo-oxidized.

Light of the desired wavelengths may be generated not only from the mercury lamp, but also from lamps filled with gases such as Xe and $H_2$.

Tests were run to determine the optimum spacing, if any, of the gap adjacent the surface of the lamp through which the gas passes. It was determined that 0.125 inches is the optimum spacing for this gap. At a standard flow rate, photo-oxidation by the reactor dropped off if the gap was made either smaller or greater than 0.125 inches. By decreasing the gap to 0.0625 inches or increasing the gap to 0.1875 inches, the ability to photo-oxidize had dropped off considerably. Thus a gap of 0.0625 to 0.1875 inches is considered to be the preferred gap size with 0.125 inches being the optimal size to allow full photo-oxidation at the fastest flow rate.

Additionally, during the testing, it was found that certain unexplained inconsistencies occurred from time to time in the amount of photo-oxidation that took place. In investigating the conditions under which these inconsistencies took place, it was noted that the sample air in all cases was of low moisture content. Subsequent testing along these lines established that, for proper photo-oxidation by the reactor, the sample gas must have a minimum moisture content of 2% saturated vapor pressure. The amount of photo-oxidation at a constant flow rate through the reactor fluctuated by 30% as the moisture content of the sample being used was varied between 0% and 2% saturated vapor pressure. Once this minimum moisture level was achieved, however, additional moisture did not change the photo-oxidation rate. To assure this minimal moisture level, a moisturizer 80 constructed as in FIG. 5 was positioned ahead of the reactor 46 in the apparatus of FIG. 4.

Figure 5:
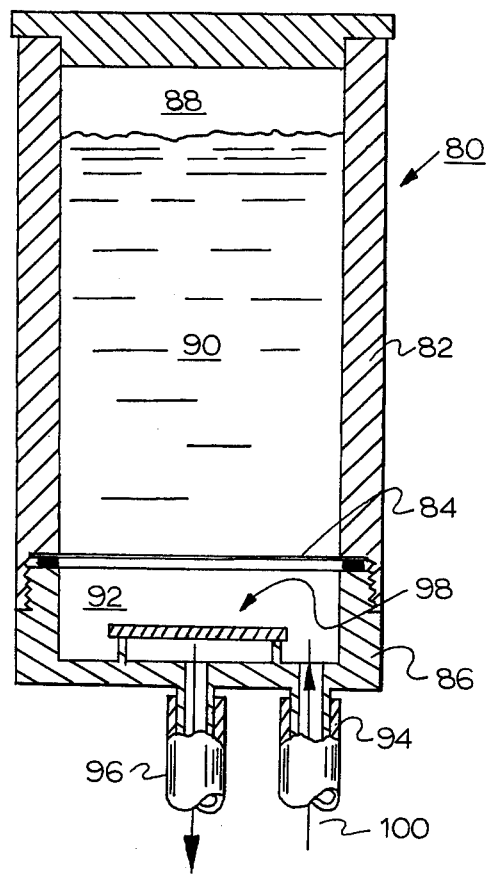
FIG. 5 is a cross section of a humidifier for use with the reactor of the present invention.

Referring to FIG. 5, the moisturizer 80 comprises a cylindrical body 82 having a porous polytetrafluoroethylene membrane 84 held securely in place across the bottom thereof by a cap 86 to form a first enclosure 88 on top of membrane 84 for containing water 90 and a second enclosure 92 under membrane 84. Cap 86 contains an inlet 94 and an outlet 96 as well as a particulate filter 98 disposed between inlet 94 and outlet 96 such that a sample gas 100 entering moisturizer 80 through inlet 94, passes through the constant volume of second enclosure 92 adjacent membrane 84 whereby its moisture content is increased to at least the 2% saturated vapor pressure minimum, then through particulate filter 98, and out outlet 96. Other methods and apparatus could, of course, be used to provide the minimum moisture content to the sample gas. The disclosed moisturizer of FIG. 5 merely offers a novel solution to this requirement for proper operation of the reactor of the present invention.

Having thus described our invention, we claim:

1. The method of measuring the quantity of methane in a gas sample comprising the steps of:
    a. passing the gas sample through an enclosed space having a source therein emitting light energy including wavelengths approaching but not less than 147 nm at a flow rate sufficiently slow to cause any hydrocarbon molecules in the gas sample to attain a superactive state;
    b. exposing the gas sample containing said superactive hydrocarbon molecules to ozone in excess for a time sufficient to photo-oxidize all non-methane hydrocarbons and photo-oxidize any methane in a known proportional amount;
    c. measuring the quantity of hydrocarbons in the photo-oxidized gas sample whereby the quantity of methane in the photo-oxidized gas sample is determined; and,
    d. rescaling the quantity measured in step (c) as a function of the proportional photo-oxidation of methane effected in step (b) whereby the quantity of methane in the original un-photo-oxidized gas sample is determined.

2. The method of measuring the quantity of methane in a gas sample as claimed in claim 1 and additionally:
    adding moisture to the gas sample prior to said step of passing the gas sample through an enclosed space having a source therein emitting light energy whereby the gas sample will contain a minimum moisture level of 2% saturated vapor pressure.

3. The method of measuring the quantity of methane in a gas sample as claimed in claim 1 wherein:
    said steps of passing the gas sample through an enclosed space whereby any hydrocarbon molecules are caused to attain a superactive state and exposing said superactive hydrocarbon molecules to ozone occur simultaneously.

4. The method of measuring the quantity of methane in a gas sample as claimed in claim 3 wherein said step of exposing of said superactive hydrocarbon molecules to ozone is accomplished by:
    a. mixing a source of oxygen with the gas sample; and,
    b. subjecting said oxygen to light energy of wavelengths capable of photolyzing said oxygen into ozone.

5. The method of removing the effects of hydrocarbons in a gas sample to be analyzed for components comprising the steps of:
    a. passing the gas sample through an enclosed space having a source therein emitting light energy of wavelengths approaching but not less than 147 nm at a flow rate sufficiently slow to cause any hydrocarbon molecules in the gas sample to attain a superactive state; and,
    b. exposing the gas sample containing said superactive hydrocarbon molecules to ozone in excess for a time sufficient to photo-oxidize said superactive hydrocarbon molecules.

6. The method of removing the effects of hydrocarbons in a gas sample as claimed in claim 5 and additionally:
    adding moisture to the gas sample prior to said step of passing the gas sample through an enclosed space having a source therein emitting light energy whereby the gas sample will contain a minimum moisture level of 2% saturated vapor pressure.

7. The method of removing the effects of hydrocarbons in a gas sample as claimed in claim 5 wherein:
    said steps of passing the gas sample through an enclosed space whereby any hydrocarbon molecules are caused to attain a superactive state and exposing said superactive hydrocarbon molecules to ozone occur simultaneously.

8. The method of removing the effects of hydrocarbons in a gas sample as claimed in claim 7 wherein said step of exposing of said superactive hydrogen molecules to ozone is accomplished by:
    a. mixing a source of oxygen with the gas sample; and,
    b. subjecting said oxygen to light energy of wavelengths capable of photolyzing said oxygen into ozone.

9. Apparatus for detecting the quantity of a specific component in a gas sample and including contaminant rejection means comprising:
    a. a reactor capable of photo-oxidizing any contaminants in the gas sample and having an input thereto and an output therefrom;
    b. valve means having a first input, a second input and an output wherein in one position said first input is connected to said output and in a second position said second input is connected to said output;

c. gas sampling means;

d. first connection means interconnecting said gas sampling means to said input of said reactor and to said first input of said valve means;

e. second connection means interconnecting said output of said reactor to said second input of said valve means;

f. means for detecting, measuring and displaying the quantity of the specific component having input means for a sample thereto; and, g. third connection means interconnecting said output of said valve means to said input means of said detecting, measuring and display means whereby when said valve means is in said first position the gas sample will bypass said reactor and when said valve means is in said second position the gas sample will pass through the reactor.

10. The apparatus of claim 9 and additionally:

means for controlling the flow rate through said reactor when said valve means is in said second position.

11. The apparatus of claim 9 wherein:

said reactor includes lamp means formed in part of a high purity quartz emitting light rich in 184.9 nm wavelengths and including wavelengths approaching but not less than 147 nm whereby said latter wavelengths will superactivate the molecules of the contaminants in the gas sample and said 184.9 nm wavelengths will convert oxygen in the gas sample to ozone to combine with said superactivated molecules.

12. The apparatus of claim 9 and additionally:

means for adding moisture to the gas sample to at least the 2% saturated vapor pressure level disposed in series with said input to said reactor whereby any gas sample entering said reactor will first pass through said moisturizer.

13. The apparatus of claim 12 wherein said means for adding moisture comprises:

a. a container for water having an opening disposed to be below the surface of water contained therein;

b. a porous membrane covering said opening; and, c. an enclosure disposed on the outside of said container adjacent said membrane whereby water vapor can pass through said membrane from said container into said enclosure, said enclosure having an inlet thereto and an outlet therefrom.

14. The apparatus of claim 13 and additionally:

a particulate filter disposed within said enclosure across said outlet.

* * * * *